(12) United States Patent
Lebofsky (10) Patent No.: US 11,603,556 B2
(45) Date of Patent: Mar. 14, 2023

(54) CELL BARCODING FOR SINGLE CELL SEQUENCING

(71) Applicant: Bio-Rad Laboratories, Inc., Hercules, CA (US)

(72) Inventor: Ronald Lebofsky, Berkeley, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 224 days.

(21) Appl. No.: 17/087,952

(22) Filed: Nov. 3, 2020

(65) Prior Publication Data

US 2021/0130880 A1   May 6, 2021

Related U.S. Application Data

(60) Provisional application No. 62/930,288, filed on Nov. 4, 2019.

(51) Int. Cl.
| | |
|---|---|
| *C12Q 1/68* | (2018.01) |
| *C12Q 1/6834* | (2018.01) |
| *C12Q 1/6855* | (2018.01) |

(52) U.S. Cl.
CPC ......... *C12Q 1/6834* (2013.01); *C12Q 1/6855* (2013.01); *C12Q 2563/137* (2013.01); *C12Q 2565/1015* (2013.01)

(58) Field of Classification Search
CPC ...................................................... C12Q 1/68

USPC .......................................................... 435/6.1
See application file for complete search history.

(56) References Cited

U.S. PATENT DOCUMENTS

| | | | | |
|---|---|---|---|---|
| 2019/0177800 A1* | 6/2019 | Boutet | ................ | C12Q 1/6804 |
| 2020/0087707 A1* | 3/2020 | Engreitz | .............. | C12Q 1/6804 |
| 2021/0388447 A1* | 12/2021 | Gartner | ................ | C12Q 1/6886 |

FOREIGN PATENT DOCUMENTS

| | | |
|---|---|---|
| WO | 2010/118235 A1 | 10/2010 |
| WO | 2020/206285 A1 | 10/2020 |

OTHER PUBLICATIONS

International Search Report and Written Opinion from PCT Appln. PCT/US2020/058654 dated Mar. 31, 2021; 13 pages.
Cusanovich, D.A. et al.; "Multiplex single-cell profiling of chromatin accessibility by combinatorial cellular indexing"; *Science*; vol. 348, Issue 6237; May 22, 2015; pp. 910-914.

* cited by examiner

*Primary Examiner* — Aaron A Priest
(74) *Attorney, Agent, or Firm* — Kilpatrick Townsend and Stockton LLP (57) ABSTRACT

Methods and compositions for attaching cell-specific barcodes without formation of partitions is provided.

20 Claims, 4 Drawing Sheets

Specification includes a Sequence Listing.

SEQUENCE LISTING

```
<160> NUMBER OF SEQ ID NOS: 8

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcgtcggcag cgtc                                                          14

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtctcgtggg ctcgg                                                         15
```

```
<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agatgtgtat aagagacag                                                    19

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcgtcggcag cgtcagatgt gtataagaga cag                                    33

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtctcgtggg ctcggagatg tgtataagag acag                                   34

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtaacgatcc agctgtcact tggaattctc gggtgccaag g                           41

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccttggcacc cgagaattcc a                                                 21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agtgacagct ggatcgttac                                                   20
```

CELL BARCODING FOR SINGLE CELL SEQUENCING

CROSS-REFERENCES TO RELATED APPLICATIONS

The present application claims priority to U.S. Provisional Application No. 62/930,288, entitled "CELL BARCODING FOR SINGLE CELL SEQUENCING" and filed Nov. 4, 2019, the entire contents being incorporated herein by reference for all purposes.

REFERENCE TO SUBMISSION OF A SEQUENCE LISTING AS A TEXT FILE

The Sequence Listing written in file 094868-1212543-117410US_SL.txt created on Jan. 4, 2021, 2,160 bytes, machine format IBM-PC, MS-Windows operating system, is hereby incorporated by reference in its entirety for all purposes.

BACKGROUND OF THE INVENTION

Current droplet microfluidic approaches achieve thousands of cells throughput.

However, larger numbers can be difficult to achieve. Using microfluidics, there are at least three factors that contribute to cell suspension dead volume and, therefore, a loss of cells for analysis: 1) leftover liquid in the inlet of the microfluidic device 2) leftover liquid in the microfluidic channels pre-partitioning and 3) material not collected from the outlets of the microfluidic device. Moreover, very large droplet emulsion volumes, corresponding to higher cell throughput experiments, are difficult to generate in a timely fashion due to the volumes required. This may have a negative impact on cell viability and labile nucleic acid substrates contained within cells, such as RNA. Lastly, when larger droplet emulsions are generated, their increased volume makes it difficult to load a single emulsion into a single tube compatible with a thermal cycler, thus further limiting large emulsion volume implementation.

Single-cell barcoding platforms require costly microfluidics (chips, oils, and instruments) and barcode beads. Instrumentation also requires costly field service engineers for maintenance and to resolve hardware issues.

Although droplet microfluidics improve scalability, only one solution add is readily supported unless more complicated on-chip droplet merging and picoinjection functionalities are used.

Labeling cells directly with oligonucleotides is an option to using oligo-conjugated beads. However, the maximum number of oligonucleotides loaded onto a cell without disrupting cell physiology is approximately 1-10 million. In droplets that are nL in size, the final concentration of oligonucleotides will often not be sufficient to drive molecular biology reactions hence preventing droplet compatibilities with direct oligonucleotide-labeled cells.

BRIEF SUMMARY OF THE INVENTION

A high density of oligonucleotides ranging up to $10^6$ to $10^7$ molecules can be attached to cells by a variety of methods. For example, cells can be labeled by cell-specific oligonucleotide-conjugated antibodies (Stoeckius et al 2018, *Genome Biology*) or by lipid-modified oligonucleotides (McGinnis et al 2019, *Nature Methods*). Oligonucleotide cell attachment creates the possibility of building cell barcodes directly on the cell, for example, by split pool barcode construction (Fan et al 2015, *Science*). These cell barcodes could, in turn, be used to barcode the nucleic acid substrates from the targeted cell.

Previously, one requirement for this form of cell barcoding was that the cell, together with the complement of the attached cell barcode oligonucleotides, had to be confined to a partition prior to oligonucleotide cleavage or release from the cell, at which point attachment to the cellular nucleic acid substrate could occur. Although droplets provide a partitioning format for this type of reaction, there are some drawbacks. First, the upper limit to the number of droplets in a single emulsion is approximately 1-2 million. To minimize multiple cells co-localizing to single droplets, cells can be loaded at lambdas of approximately 0.05-0.1. Based on the number of droplets per emulsion, the number of cells encapsulated is limited to 50,000 to 100,000, maximally. This cell throughput may not be sufficient for some types of experiments and suffers from upwards scalability limits. Second, due to cell suspensions leftover in the inlet, the microfluidics and in droplets not harvested from the outlet, cell loss using droplet microfluidics is difficult to eliminate resulting in cell utilization of approximately 60-85%. For precious cells, this level of cell utilization may not be sufficient. Third, droplet microfluidics require chips, oils, and instruments, which are all expensive and difficult to support. Fourth, adding reagents to already formed droplets and washing the products while still maintaining droplets is not easily engineered, albeit feasible through picoinjection, droplet merging and magnetic bead trapping approaches. This constraint makes single-cell DNA analysis difficult since proteinase K digestion followed by inactivation and then biochemistry addition is not supported by simple droplet microfluidics. Fifth, since only 1-10 million oligonucleotides can be loaded onto cells without disrupting their membrane, droplets have to be tens of pL in volume to provide sufficient oligo concentrations to drive molecular biology reactions. These small droplets may be difficult to achieve with two aqueous inlet microfluidics. Sixth, cells usually have to be washed to remove their media prior to barcoding reactions. This contributes significantly to cell loss.

The present methods solve the above limitations with droplets as follows: Subsequent to building the cell barcodes on cells, the cells are resuspended with hydrogel solution that is density matched for the cells such that cells do not settle. This can be achieved with common reagents used to keep cells in suspension such as sucrose cushions, Percoll (Sigma) and/or Optiprep (Sigma). The solidification of the hydrogel then ensues. The mechanism behind solidification depends on the material used for the hydrogel. For example, agarose solidification would be caused by a drop in temperature. Alternatively, alginate can be crosslinked using calcium. Alternatively, TEMED initiates the crosslinking of polyacrylamide monomers. The cells are thus dispersed throughout the solidified hydrogel matrix.

The hydrogel may or not be modified to bind the cell barcode oligonucleotide. For example, the cell barcode oligonucleotide can be modified at the 5' end with biotin, and an avidin analog such as streptavidin, can be conjugated to the hydrogel material. Thus, when in solution, the cells with the bound oligonucleotides will move freely, however, once the hydrogel solidifies any released oligonucleotides will bind to the matrix in the direct vicinity of the cell membrane to form a skin or shell where the cell membrane exists. Hydrogels that are between 0.01 to 10% wt/vol for example are porous to ionic and non-ionic detergents, as well as low molecular weight proteins, enzymes, and co-factors. Thus after trapping the cells in the hydrogel matrix, cell lysis reagents (e.g., 0.1% NP-40) can be applied to the cells. The lysis reagents will diffuse through the matrix and lyse the cells. Cell barcode oligonucleotide cleavage or release will occur either as a direct result of cell lysis and membrane dissolution or through a specific or non-specific agent that cleaves or releases the oligonucleotide from the cell. The released cell-substrate nucleic acids will then bind to the cell barcodes oligonucleotides that have been immobilized into a shell at the cell membrane/hydrogel interface.

The volume of the area encircled by the cell/hydrogel interface is essentially the volume of the cell. This minimal volume will significantly increase the effective concentration of the cell barcode oligonucleotides to a maximum value whether they are immobilized to the shell of oligonucleotides or not. This can compensate, for example, for the limited number of cell barcode oligonucleotides that can be loaded onto cells without affecting their physiology, e.g., 1-10 million oligonucelotides per cell. For cells that are approximately 9 microns in diameter, the effective concentration with 2 million oligonucleotides would be several hundred nM, which is a concentration sufficient to support most molecular biology reactions, such as reverse transcription. Low molecular weight RNA or DNA dependent polymerases can either be added together with the lysis reagent or after and this may also be subsequent to an intervening wash to remove or inactivate the cell lysis reagent.

Once cell barcoding occurs as a result of cell barcode oligonucleotide tagging of the cellular substrate nucleic acid, the final steps of library prep can occur either in the hydrogel matrix or in solution after removing the material from the hydrogel matrix that has or has not been solubilized. For example, reverse transcriptase, due to its low molecular weight size, will flow through hydrogels of up to 5% in composition. Applying this with the lysis reagent together with or without an oligonucleotide cleavage/release agent would lead to the following events. As the cell membrane dissolves with the lysis reagent, the cell barcode oligonucleotides will bind to the hydrogel to form a shell where the cell membrane existed. Released RNA will bind to the immobilized oligonucleotides at the shell where the cell membrane existed and reverse transcriptase will synthesize cDNA. This is the barcoding reaction. Once this occurs, the hydrogel can be dissolved and final steps to prepare the NGS library can be done in bulk.

None of the above workflows require microfluidics (chips, oils, and instruments) and occurs in bulk. One benefit of this format is that multi-step reactions can be supported. For example, if DNA genotype information is wanted, the first reagent to flow through the hydrogel could be proteinase K, for example, thermo-sensitive proteinase K. This will digest the nucleosomes and chromatin accessory proteins leaving the DNA accessible to further molecular biology. Through the destruction of the cell membrane the cell barcode oligonucleotides can bind to form a shell where the cell membrane existed. Proteinase K can be deactivated, DNA polymerase together with reagents can flow into the hydrogel and barcoding through template-directed DNA synthesis, for example, can occur. Once barcoded, the final steps for library preparation can occur either inside or outside the hydrogel.

Cells in their native media can be mixed with the hydrogel material. Once solidified, the hydrogel can be washed to remove the media. Furthermore, since each cell will have a cell barcode clonal set of oligonucleotides, each cell captured in the hydrogel matrix will be barcoded. These two factors will increase cell utilization from the starting material to close to 100%.

In some aspects, a mixture of individual cells or individual cell nuclei and cross-linked hydrogel is provided. In some embodiments, the individual cells comprise heterologous oligonucleotides attached to cell membranes of the individual cells or the individual cell nuclei comprise heterologous oligonucleotides attached to nuclear membranes of the individual cell nuclei.

In some embodiments, the individual cells comprise heterologous oligonucleotides anchored in cell membranes of the individual cells or the individual cell nuclei comprise heterologous oligonucleotides anchored in nuclear membranes of the individual cell nuclei. In some embodiments, the heterologous barcoded oligonucleotides comprise a lipid moiety and wherein the lipid moiety anchors the heterologous barcoded oligonucleotides in the cell membranes.

In some embodiments, the hydrogel is covalently linked to a molecule having binding affinity for the heterologous oligonucleotides. In some embodiments, the hydrogel is non-covalently linked to a molecule having binding affinity for the heterologous oligonucleotides. In some embodiments, the molecule is selected from the group consisting of biotin, streptavidin, an antibody, an aptamer, nickel (Ni), europium (Eu) or a polynucleotide comprising a sequence of at least 6 contiguous nucleotides that is fully complementary to a sequence in the heterologous barcoded oligonucleotides.

In some embodiments, the cells are mammalian cells. In some embodiments, the nuclei or cells comprise fragmented nuclear DNA, wherein the fragmented DNA comprises common adapter sequences at ends of the fragments.

In some embodiments, the hydrogel comprises alginate, agarose, polyacrylamide, chitosan, hyaluronan, dextran, collagen, fibrin, polyethylene glycol (PEG), poly(hydroxyethyl methacrylate) (polyHEMA), polyvinyl alcohol (PVA) or polycaprolactone (PCL).

In some embodiments, the heterologous barcoded oligonucleotides comprise a cell-specific barcode sequence and a 3' sequence. In some embodiments, the 3' sequence is a polyT sequence of at least 5 contiguous thymines. In some embodiments, the 3' sequence is a random sequence of at least 5 (e.g., at least 8, at least 10, at least 12, e.g., 6-30) contiguous nucleotides. In some embodiments, the 3' sequence is a target gene-specific sequence of at least 5 contiguous nucleotides. In some embodiments, the 3' sequence is an adapter of at least 5 (e.g., 5-100, 5-25) contiguous nucleotides. In some embodiments, the adapter can be complementary to common adapter sequences at the end of fragmented DNA from the cell or nuclei for example.

In some embodiments, the heterologous barcoded oligonucleotides further comprise a 5' PCR handle sequence.

In some aspects, a method of tagging cell-specific barcodes to cell nucleic acids is provided. In some embodiments, the method comprises: providing (i) cells or isolated cell nuclei having heterologous barcoded oligonucleotides attached to cell membranes of the cells or (ii) cell nuclei comprising heterologous oligonucleotides attached to nuclear membranes of the individual cell nuclei; mixing the cells or nuclei with a liquid-form hydrogel; cross-linking the hydrogel around the cells or nuclei, wherein the hydrogel forms a solid gel; releasing the heterologous barcoded oligonucleotides from the cell membranes or nuclear membranes to generate released heterologous barcoded oligonucleotides; allowing the heterologous barcoded oligonucleotides released from the cell membranes or nuclear membranes to locate at solidified hydrogel surrounding the cells or nuclei; attaching the heterologous barcoded oligonucleotides to cell polynucleotides or copies or cDNAs thereof to form barcoded cell polynucleotides; and dissolving the solidified hydrogel or extracting the barcoded cell polynucleotides from the solidified hydrogel, thereby releasing barcoded cell polynucleotides from the hydrogel, thereby tagging cell-specific barcodes to cell nucleic acids.

In some embodiments, the allowing comprises binding the heterologous barcoded oligonucleotides released from the cell membranes or nuclear membranes to the solidified hydrogel surrounding the cells or nuclei. In some embodiments, the allowing comprises diffusion of the heterologous barcoded oligonucleotides released from the cell membranes or nuclear membranes to the solidified hydrogel surrounding the cells or nuclei such that the heterologous barcoded oligonucleotides are localized at a hydrogel/membrane interface. In some embodiments, the extracting the barcoded cell polynucleotides from the solidified hydrogel comprises electrophoresing the barcoded cell polynucleotides from the solidified hydrogel.

In some embodiments, the method further comprises sequencing the barcoded cell polynucleotides released from the hydrogel.

In some embodiments, the heterologous barcoded oligonucleotides comprise a lipid moiety and wherein the lipid moiety anchors the heterologous barcoded oligonucleotides in the cell membranes or nuclear membranes.

In some embodiments, the hydrogel is covalently linked to a molecule having binding affinity for the heterologous oligonucleotides. In some embodiments, the molecule is selected from the group consisting of biotin, streptavidin, an antibody, an aptamer, Ni, Eu, or a polynucleotide comprising a sequence of at least 6 contiguous nucleotides that is fully complementary to a sequence in the heterologous barcoded oligonucleotides.

In some embodiments, the cells are mammalian cells.

In some embodiments, the nuclei or cells comprise fragmented nuclear DNA, wherein the fragmented DNA comprises common adapter sequences at ends of the fragments. In some embodiments, the method further comprises fragmenting the nuclear DNA and introducing the common adapter sequence with a transposase (e.g., via tagmentation).

In some embodiments, the hydrogel comprises alginate, agarose, polyacrylamide, chitosan, hyaluronan, dextran, collagen, fibrin, polyethylene glycol (PEG), poly(hydroxyethyl methacrylate) (polyHEMA), polyvinyl alcohol (PVA) or polycaprolactone (PCL). In some embodiments, the hydrogel comprises alginate and the crosslinking comprises contacting the hydrogel with calcium. In some embodiments, the hydrogel is covalently linked to a molecule having binding affinity for the heterologous barcoded oligonucleotides and the released heterologous barcoded oligonucleotides bind to the molecule at a hydrogel/cell interface or hydrogel/nuclei interface. In some embodiments, the molecule is streptavidin and the heterologous barcoded oligonucleotides biotinylated. In some embodiments, the molecule is a polynucleotide comprising a sequence of at least 6 contiguous nucleotides that is fully complementary to a sequence in the heterologous barcoded oligonucleotides such that the polynucleotide linked to the hydrogel hybridizes to the released heterologous barcoded oligonucleotides.

In some embodiments, the releasing comprises lysing the cells or nuclei. In some embodiments, the lysing comprising contacting the cells or nuclei in the hydrogel with an ionic or non-ionic detergent. In some embodiments, the lysing comprising contacting the cells to a protease (for example, proteinase K).

In some embodiments, the releasing comprises cleaving the heterologous barcoded oligonucleotides from a portion of the oligonucleotides to free the heterologous barcoded oligonucleotides from the cell membrane or nuclear membrane.

In some embodiments, the attaching comprises ligating the heterologous barcoded oligonucleotides to cell polynucleotides or copies or cDNAs thereof to form the barcoded cell polynucleotides.

In some embodiments, the attaching comprises hybridizing at least the 3' end of the heterologous barcoded oligonucleotides to cell polynucleotides or copies or cDNAs thereof. In some embodiments, the method further comprises extending the 3' end in a template-specific manner with a polymerase to form the barcoded cell polynucleotides.

In some embodiments, after the lysing and before the attaching the method comprises contacting the cells with a reverse transcriptase under conditions to form cDNAs from RNA in the cells; and the attaching comprises attaching the heterologous barcoded oligonucleotides to the cDNAs.

In some embodiments, the heterologous barcoded oligonucleotides comprise barcode sequences that are unique for the cells or nuclei to which the heterologous barcoded oligonucleotides are attached.

In some embodiments, the providing comprises synthesizing the heterologous barcoded oligonucleotides on the cells or nuclei using a split and pool methodology such that different cells or different nuclei are linked to a plurality of identical heterologous barcoded oligonucleotides and where different cells or different nuclei have unique heterologous barcoded oligonucleotides.

In some embodiments, the heterologous barcoded oligonucleotides comprise a cell-specific barcode sequence and a 3' sequence. In some embodiments, the 3' sequence is a polyT sequence of at least 5 contiguous thymines. In some embodiments, the 3' sequence is a random sequence of at least 5 contiguous nucleotides. In some embodiments, the 3' sequence is a target gene-specific sequence of at least 5 (e.g., at least 8, at least 10, at least 12, e.g., 6-30) contiguous nucleotides. In some embodiments, the 3' sequence is an adapter of at least 5 (e.g., 5-100, 5-25) contiguous nucleotides. In some embodiments, the adapter can be complementary to common adapter sequences at the end of fragmented DNA from the cell or nuclei for example. In some embodiments, the heterologous barcoded oligonucleotides further comprise a 5' PCR handle sequence.

BRIEF DESCRIPTION OF THE DRAWINGS

FIG. 1 discloses "GTAACGATCCAGCTGTCACTTG-GAATTCTCGGGTGCCAAGG" as SEQ ID NO: 6, "CCTTGGCACCCGAGAATTCCA" as SEQ ID NO: 7, and "AGTGACAGCTGGATCGTTAC" as SEQ ID NO: 8.

FIG. 2 discloses "GTAAC-GATCCAGCTGTCACTTGGAATTCTCGGGTGC-CAAGG" as SEQ ID NO: 6, "CCTTGGCACCCGAGAAT-TCCA" as SEQ ID NO: 7, and "AGTGACAGCTGGATCGTTAC" as SEQ ID NO: 8.

FIG. 3B continues from FIG. 3A.

DEFINITIONS

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a bead" includes a plurality of such beads and reference to "the sequence" includes reference to one or more sequences known to those skilled in the art, and so forth.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2nd ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "barcode" refers to a short nucleotide sequence (e.g., at least about 2, 3, 4, 6, 8, 10, 12, 14, 16, 20, 25 or more (e.g., 4-30, 5-25, 5-20) nucleotides long) that identifies a molecule to which it is conjugated. Barcodes can be used, e.g., to identify molecules in a cell or nucleus. Such a cell-specific or nucleus-specific barcode should be unique for that cell or nucleus as compared to barcodes present in other cells or nuclei. Once associated with a cell-specific or nucleus-specific barcode, nucleic acids from each cell can be distinguished from nucleic acid of other cells due to the unique barcode. In some cases, the cell-specific or nucleus-specific barcode is generated using a split and mix (also referred to as split and pool) synthetic scheme.

Additional types of barcodes can also be included in a polynucleotide having a cell-specific or nucleus-specific barcode. For example, additional barcodes can uniquely identify the molecule to which it is conjugated. Such barcodes are useful for determining the number of original molecule sin a sample for instance.

The length of the barcode sequence determines how many unique samples can be differentiated. For example, a 1 nucleotide barcode can differentiate 4, or fewer, different samples or molecules; a 4 nucleotide barcode can differentiate $4^4$ or 256 samples or less; a 6 nucleotide barcode can differentiate 4096 different samples or less; and an 8 nucleotide barcode can index 65,536 different samples or less.

Barcodes can be synthesized and/or polymerized (e.g., amplified) using processes that are inherently inexact. Thus, barcodes that are meant to be uniform (e.g., a cell-specific barcode shared amongst all barcoded nucleic acid of a cell) can contain various N−1 deletions or other mutations from the canonical barcode sequence. Thus, barcodes that are referred to as "identical or substantially identical copies" can include barcodes that differ due to one or more errors in, e.g., synthesis, polymerization, or purification and thus contain various N−1 deletions or other mutations from the canonical barcode sequence. Moreover, the random conjugation of barcode nucleotides during synthesis using e.g., a split and pool approach and/or an equal mixture of nucleotide precursor molecules as described herein, can lead to low probability events in which a barcode is not absolutely unique (e.g., different from other barcodes of a population or different from barcodes of a different partition, cell, or bead). However, such minor variations from theoretically ideal barcodes do not interfere with the single cell analysis methods, compositions, and kits described herein. Therefore, as used herein, the term "unique" in the context of a particle, cellular, partition-specific, or molecular barcode encompasses various inadvertent N−1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is known in the art, see for example Katsuyuki Shiroguchi, et al. Proc Natl Acad Sci USA., 2012 Jan. 24; 109(4):1347-52; and Smith, A M et al., Nucleic Acids Research (2010), 38(13):e142.

The term "amplification reaction" refers to any in vitro method for multiplying the copies of a target sequence of nucleic acid in a linear or exponential manner. Such methods include, but are not limited to, polymerase chain reaction (PCR); DNA ligase chain reaction (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3 SR); single-primer isothermal amplification (SPIA), loop mediated isothermal amplification (LAMP), strand displacement amplification (SDA); multiple displacement amplification (MDA); rolling circle amplification (RCA); as well as others known to those of skill in the art. See, e.g., Fakruddin et al., J. Pharm Bioallied Sci. 2013 5(4):245-252.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification.

A nucleic acid, or portion thereof, "hybridizes" to another nucleic acid under conditions such that non-specific hybridization is minimal at a defined temperature in a physiological buffer. In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C.

The term "oligonucleotide" is not intended to be limited to a specific number of nucleotides. In some embodiments, an oligonucleotide can have 10-500 nucleotides, e.g., 20-200 or 15-100 nucleotides in length.

The term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel, well, tube, and plate. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used herein, "nucleic acid" means DNA, RNA, single-stranded, double-stranded, or more highly aggregated hybridization motifs, and any chemical modifications thereof.

Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C.

The term "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., PCR Protocols: A Guide to Methods and Applications, Innis et al., eds, 1990. Primers can be DNA, RNA, or a chimera of DNA and RNA portions. In some cases, primers can include one or more modified or non-natural nucleotide bases. In some cases, primers are labeled.

The term "target nucleic acid" refers to a polynucleotide such as DNA, e.g., single stranded DNA or double stranded DNA, RNA, e.g., mRNA or miRNA, or a DNA-RNA hybrid. DNA includes genomic DNA and complementary DNA (cDNA).

As used herein, the term "heterologous" refers to two components (e.g., a cell and a barcode oligonucleotide) that are not found together in nature, e.g., because they are not found together in the same wild-type organism.

The term "template nucleic acid" refers to a polynucleotide template that is used to generate a second polynucleotide strand that can be complementary to the template or a portion thereof. In some embodiments, in a reverse transcription reaction an RNA template is used to generate a DNA that is complementary to the RNA. In other embodiments, a first strand cDNA is used as a template during polymerase based amplification to generate a second stand cDNA that is complementary to the first strand.

DETAILED DESCRIPTION OF THE INVENTION

The inventors have discovered a new way of associating polynucleotide barcodes with individuals cell nucleic acids. An advantage of the methods described herein is that individual cells do not need to be inserted into droplets or other partitions, which can lead to inefficiencies of matching single cells with single partitions or other issues as described herein. Instead, embodiments described herein can involve forming a solid hydrogel around a cell mixture such that cells are separated from each other by the hydrogel, wherein the cells have cell-specific barcode oligonucleotide attached to cell membranes. Similarly, cell nuclei can alternatively be used to form a solid hydrogel with isolated nuclei separated from each other, wherein the nuclei have nuclei-specific barcode oligonucleotide attached to nuclear membranes. Regardless of whether individual cells or nuclei are used, once the cells or nuclei are embedded in the solid hydrogel, the barcode oligonucleotides can be released from the membranes. Because the cells or nuclei are embedded in the hydrogel, the barcode oligonucleotides will not diffuse beyond the interface of the cell or nucleus and the hydrogel. In some embodiments, the hydrogel can include a molecule having affinity for the barcode oligonucleotides, further maintaining the position of the barcode oligonucleotides. The cells or nuclei can then be lysed or permeabilized to allow nucleic acids (DNA, RNA or copies thereof) from the cells or nuclei to associate with the barcode oligonucleotides at the interface of the cell or nucleus and the hydrogel. The cell-specific or nucleus-specific barcode oligonucleotide is associated with the cell or nucleus nucleic acid, thereby barcoding the nucleic acids and allowing for subsequent mixing of the nucleic acids from the different cells or nuclei for analysis without losing track of the cell or nuclear origin of individual nucleic acids. This and other aspects are described herein.

Any type of cells can be used according to the methods and compositions described herein. In some embodiments, the cells are mammalian, for example human cells. In some embodiments, the cells are from a biological sample. Biological samples can be obtained from any biological organism, e.g., an animal, plant, fungus, pathogen (e.g., bacteria or virus), or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, and transformed cells, stem cells, or cells found in stool, urine, etc.

In some embodiments, isolated nuclei are provided. Methods of forming isolated nuclei are known and can be used as desired. Exemplary methods of generating isolated nuclei include those described in U.S. Pat. No. 8,546,134; Gaublomme, et al., Nature Communications volume 10, Article number: 2907 (2019). In some embodiments, the nuclei comprise fragmented nuclear DNA, allowing for example, for a variation of ATAC-seq. For example, the cells can be permeabilized and the nuclear DNA within can be fragmented, for example with a tranposase that introduces adapter sequences to the ends of the fragmented DNA. Where isolated nuclei are used, the nuclei need not be permeabilized for entry to the transposase into the nuclei. The action of the transposase sometimes referred to as "tagmentation" and can involve introduction of different adapter sequences on different sides of a DNA breakage point or the adapter sequences added can be identical. In either case, the adapter sequences are common adapter sequences in that the adapter sequences are the same across a diversity of DNA fragments. Homoadapter-loaded tagmentases are tagmentases that contain adapters of only one sequence, which adapter is added to both ends of a tagmentase-induced breakpoint in the genomic DNA. Heteroadapter-loaded tagmentases are tagmentases that contain two different adapters, such that a different adapter sequence is added to the two DNA ends created by a tagmentase-induced breakpoint in the DNA. Adapter loaded tagmentases are further described, e.g., in U.S. Patent Publication Nos: 2010/0120098; 2012/0301925; and 2015/0291942 and U.S. Pat. Nos. 5,965,443; 6,437,109; 7,083,980; 9,005,935; and 9,238,671, the contents of each of which are hereby incorporated by reference in the entirety for all purposes. By quantifying the number of intact sequencing reads (indicating heterochromatin not cleaved by transposase) one can measure chromatin structure.

A tagmentase is an enzyme that is capable of forming a functional complex with a transposon end-containing composition and catalyzing insertion or transposition of the transposon end-containing composition into the double-stranded target DNA with which it is incubated in an in vitro transposition reaction. Exemplary transposases include but are not limited to modified Tn5 transposases that are hyperactive compared to wildtype Tn5, for example can have one or more mutations selected from E54K, M56A, or L372P. Wild-type Tn5 transposon is a composite transposon in which two near-identical insertion sequences (IS50L and IS50R) are flanking three antibiotic resistance genes (Reznikoff W S. Annu Rev Genet 42: 269-286 (2008)). Each IS50 contains two inverted 19-bp end sequences (ESs), an outside end (OE) and an inside end (IE). However, wild-type ESs have a relatively low activity and were replaced in vitro by hyperactive mosaic end (ME) sequences. A complex of the transposase with the 19-bp ME is thus all that is necessary for transposition to occur, provided that the intervening DNA is long enough to bring two of these sequences close together to form an active Tn5 transposase homodimer (Reznikoff W S., Mol Microbiol 47: 1199-1206 (2003)). Transposition is a very infrequent event in vivo, and hyperactive mutants were historically derived by introducing three missense mutations in the 476 residues of the Tn5 protein (E54K, M56A, L372P), which is encoded by IS50R (Goryshin I Y, Reznikoff W S. 1998. J Biol Chem 273: 7367-7374 (1998)). Transposition works through a "cut-and-paste" mechanism, where the Tn5 excises itself from the donor DNA and inserts into a target sequence, creating a 9-bp duplication of the target (Schaller H. Cold Spring Harb Symp Quant Biol 43: 401-408 (1979); Reznikoff W S., Annu Rev Genet 42: 269-286 (2008)). In current commercial solutions (Nextera™ DNA kits, Illumina), free synthetic ME adapters are end-joined to the 5'-end of the target DNA by the transposase (tagmentase). In some embodiments, the tagmentase is linked to a solid support (e.g., a bead that is different from the bead linked to the forward primer). An example commercial bead-linked tagmentase is Nextera™ DNA Flex (Illumina).

In some embodiments, the adapter(s) is at least 19 nucleotides in length, e.g., 19-100 nucleotides. In some embodiments, the adapters are double stranded with a 5' end overhang, wherein the 5' overhand sequence is different between heteroadapters, while the double stranded portion (typically 19 bp) is the same. In some embodiments, an adapter comprises TCGTCGGCAGCGTC (SEQ ID NO:1) or GTCTCGTGGGCTCGG (SEQ ID NO:2). In some embodiments involving the heteroadapter-loaded tagmentase, the tagmentase is loaded with a first adapter comprising TCGTCGGCAGCGTC (SEQ ID NO:1) and a second adapter comprising GTCTCGTGGGCTCGG (SEQ ID NO:2). In some embodiments, the adapter comprises AGATGTGTATAAGAGACAG (SEQ ID NO:3) and the complement thereof (this is the mosaic end and this is the only specifically required cis active sequence for Tn5 transposition). In some embodiments, the adapter comprises TCGTCGGCAGCGTCAGATGTGTATAAGAGACAG (SEQ ID NO:4) with the complement for AGATGTGTATAAGAGACAG (SEQ ID NO:3) or GTCTCGTGGGCTCGGAGATGTGTATAAGAGACAG (SEQ ID NO:5) with the complement for AGATGTGTATAAGAGACAG (SEQ ID NO:3). In some embodiments involving the heteroadapter-loaded tagmentase, the tagmentase is loaded with a first adapter comprising TCGTCGGCAGCGTCAGATGTGTATAAGA-GACAG (SEQ ID NO:4) with the complement for AGATGTGTATAAGAGACAG (SEQ ID NO:3) and GTCTCGTGGGCTCGGAGATGTGTATAAGAGACAG (SEQ ID NO:5) with the complement for AGATGTGTATAAGAGACAG (SEQ ID NO:3).

Figure 1:
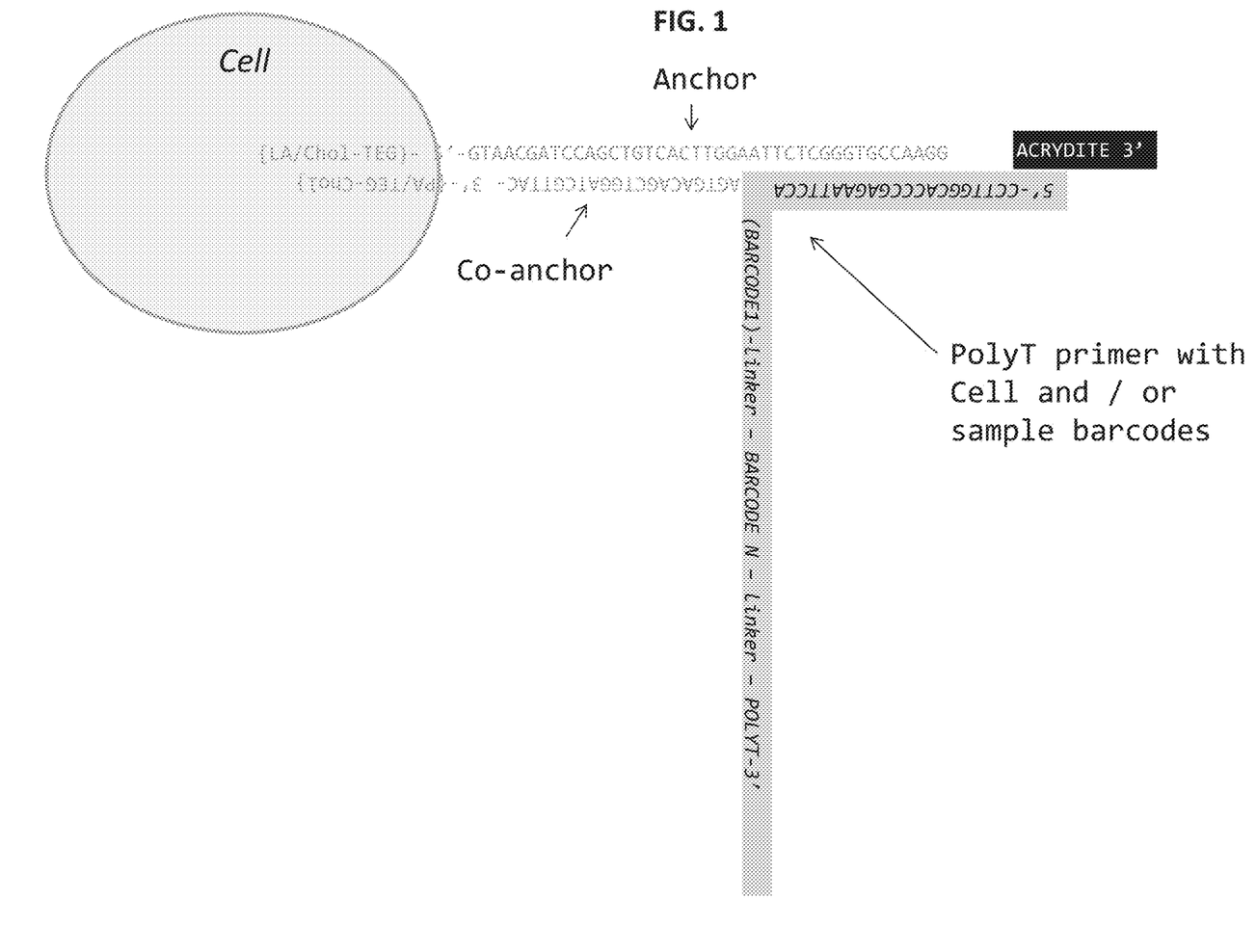
FIG. 1 depicts a lipid-modified oligonucleotide comprising a cell or sample barcode linked to a cell. An acrydite moiety is present on the 3' end of the anchor oligonucleotide.
Figure 2:
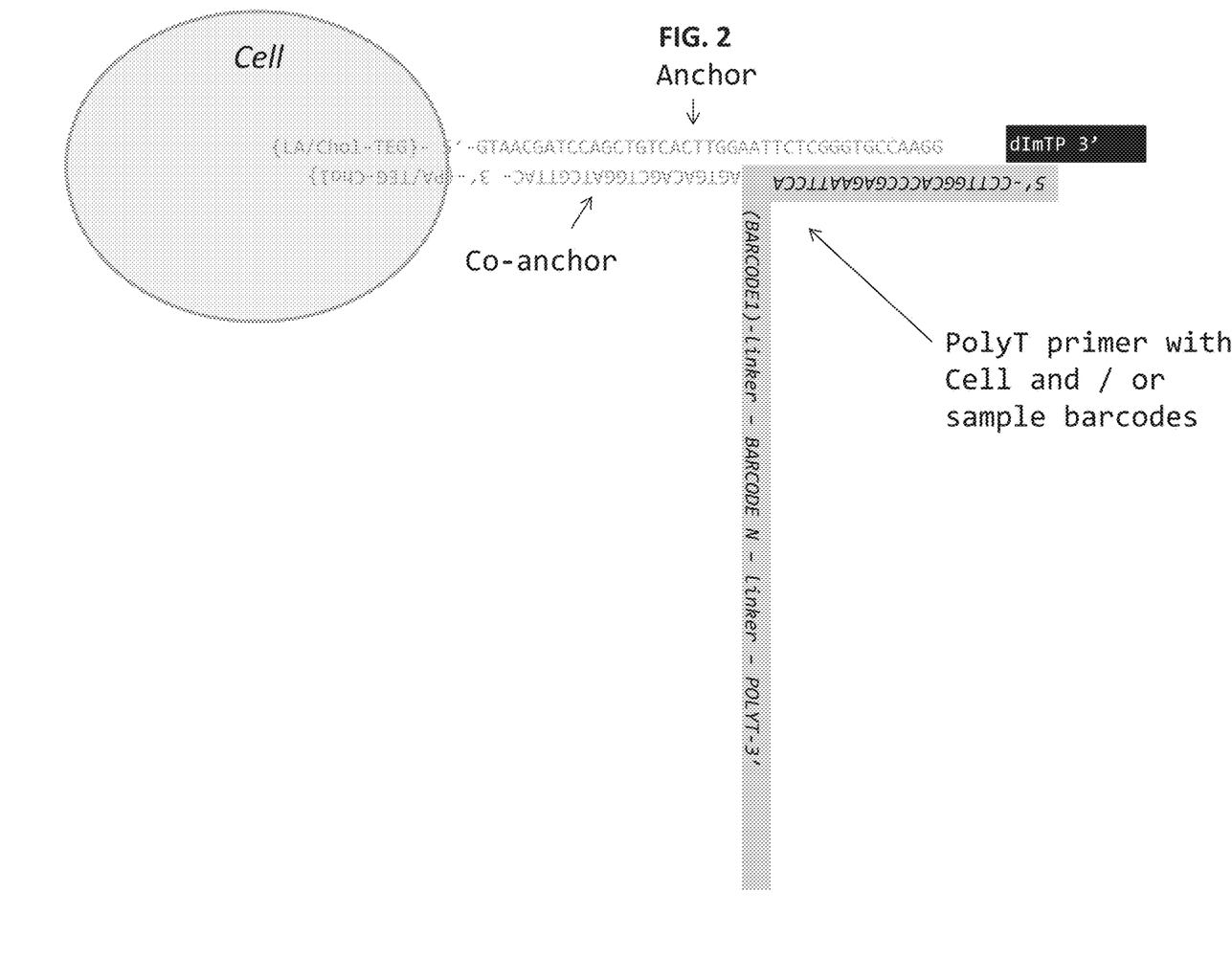
FIG. 2 depicts a lipid-modified oligonucleotide comprising a cell or sample barcode linked to a cell. Imidazole triphosphate nucleosides are present on the 3' end of the anchor oligonucleotide.
Figure 3A:
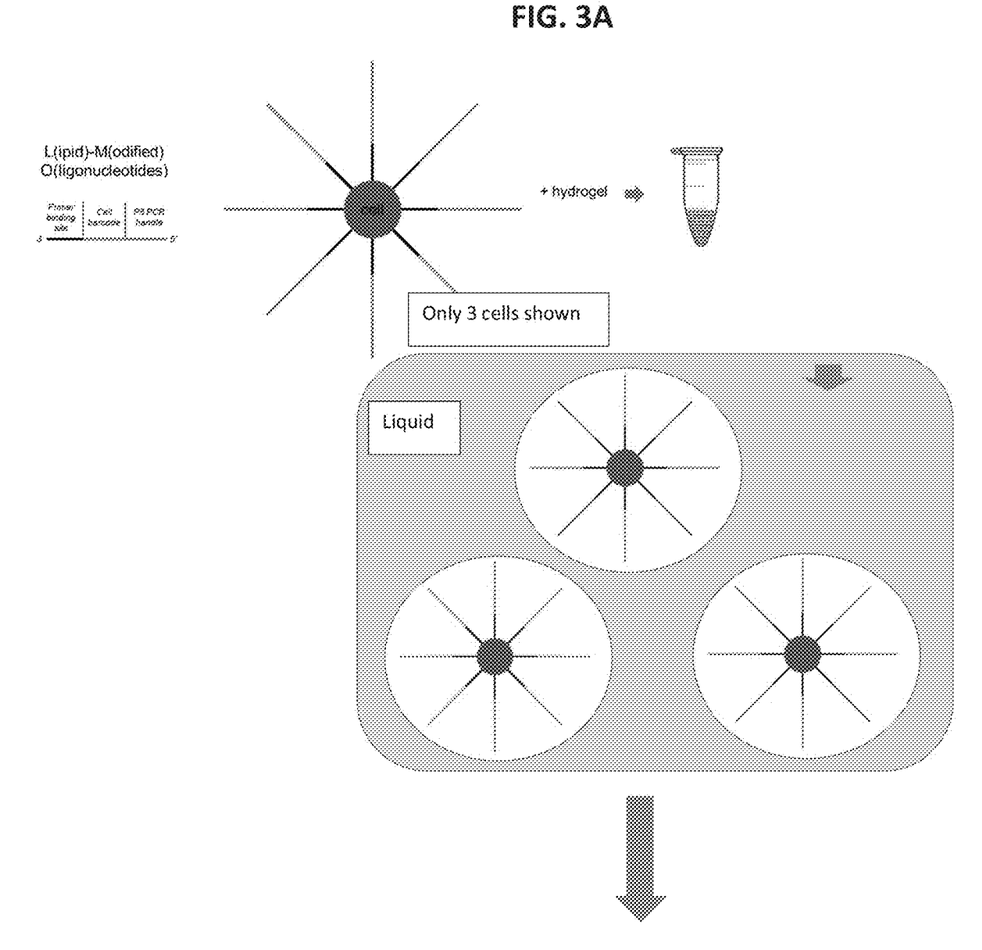
FIG. 3A-B depicts an exemplary workflow.
Figure 3B:
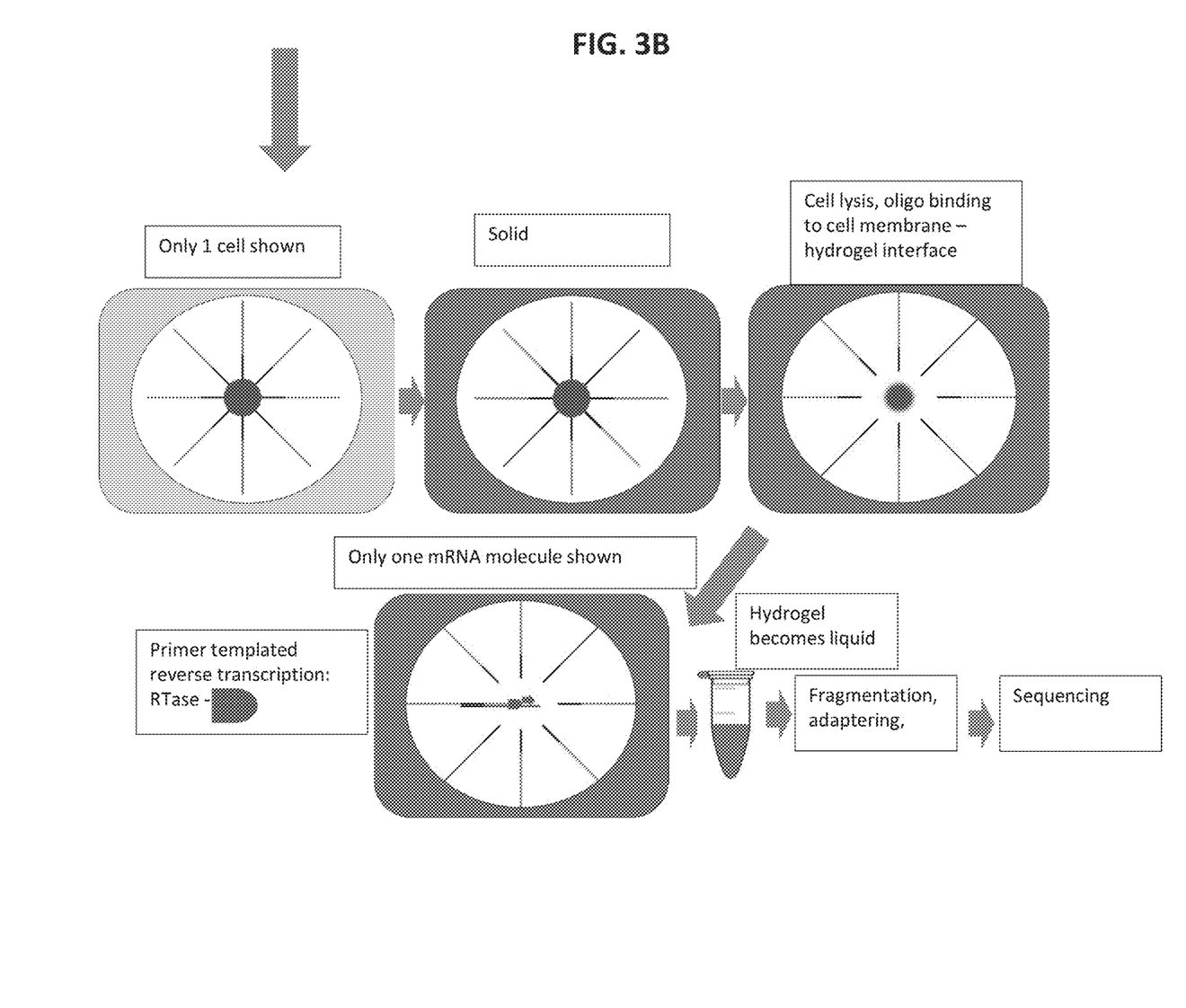

Cells or isolated nuclei can be barcoded by attaching an oligonucleotide comprising one or more barcode sequence to the cell membrane, or in the case of isolated nuclei, to the nuclear membrane. Oligonucleotides can be attached to cell or nuclear membranes in several ways. In some embodiments, lipid (LMO) or cholesterol (CMO)-modified oligonucleotides can be mixed with the cells or isolated nuclei, allowing the lipid or cholesterol to embed in the membranes. For example, in some embodiments, an anchor, co-anchor and barcode oligonucleotide are hybridized in solution (FIGS. 1 and 2 depict an example). The cholesterol or lipid-derivative ends of the anchor and co-anchor embed into the cell or nuclear membrane. Protocols for barcoding cells using LMOs or CMOs are described in, e.g., McGinnis, et al., *Nature Methods* 16:619-626 (2019); Weber et al., *Biomacromolecules* 15:4621-4626 (2014). In some embodiments, the LMOs comprise a spacer between the lipid moiety and the nucleic acid. The lipid moiety, in some embodiments, includes a long alkyl chain of 12-24 carbon atoms, e.g., 12-22, 12-20, 12-18, 14-22, 14-20, 14-18, 16-22, 16-20, or 16-18 carbon atoms. The spacer may be for example 10-80 nucleotides long, e.g., 10-60, 10-40, 20-80, 20-60, 20-40, 40-60, 40-80, 50-80, 50-80, or 60-80 nucleotides long.

In some embodiments the barcode oligonucleotide is hybridized to an oligonucleotide embedded in the cell or nuclear membrane. For example an LMO or CMO embedded in a membrane can comprise a binding sequence (for example 6-20 nucleotides in length) and an oligonucleotide comprising a barcode sequence can be hybridized to the binding sequence via a complementary sequence in the barcode oligonucleotide. In some embodiments, the 3' end of the barcode oligonucleotide is free to bind to the complementary cellular nucleic acid.

In yet another embodiment, streptavidin or other avidin analog is attached to the membrane (e.g., via lipid or cholesterol attachment) and the barcode oligonucleotides are biotinylated allowing for binding of the barcode oligonucleotides to be attached to the streptavidin attached to the membrane. In other embodiments, other affinity molecules can be linked to the barcode oligonucleotides such that the affinity molecules bind to the cell or nuclear membrane or components or proteins therein. Examples of binding molecules include but are not limited to an antibody or an aptamer. See, e.g., Stoekius, et al., *Genome Biology* 19:224 (2018); Delley, et al., *bioRxiv* 1-10 (2017). In some embodiments, the barcode oligonucleotides can be conjugated to the cells. See, e.g., Gehring, et al., *BioRxiv* 1-19 (2018). The above options for attaching barcodes to cells are intended as examples and are provided without limitation.

In some embodiments, the barcode oligonucleotides further comprise an acrydite phosphoramidite moiety at the 3' end of the oligonucleotides. See, e.g., Rehman, et al., *Nuc. Acids Res.* 27(20) 649-655 (1999).

In some embodiments, the barcode oligonucleotides further comprise imidazole triphosphate nucleosides at the 3' end of the oligonucleotides. See, e.g. Rothlisberger, et al., *Chemical Communications* 53 13031-13034.

Cell specific barcodes can be synthesized on cells or nuclei for example using a split and pool method. For example, an oligonucleotide comprising a common sequence can be attached to cell or nuclear membranes or cells or nuclei, respectively, to form a mixture of cells or nuclei having the oligonucleotide in attached to the membranes. The mixture can then be split into portions, where each portion receives a different nucleotide added to the oligonucleotide. The cells or nuclei are then combined, mixed, and split into portions again. This process if repeated, resulting in a unique, cell-specific (or nuclei-specific) nucleotide sequence on the cells or nuclei. An example of split-and-pool methods is provided in Fan, et al., *Science* 2015 Feb. 6; 347(6222):1258367. Optionally a common capture sequence can be added to the 3' end of the oligonucleotides, such that the resulting oligonucleotides include a 5' common sequence (optionally usable as a PCR handle, a cell-specific barcode, and a 3' capture sequence.

While the description here describes cell-specific barcodes it will be appreciated that other types of barcodes can equally be used where barcodes are described herein. For example, in some embodiments, cells from the same sample are all labelled with the same barcode oligonucleotide sequence, but cells from different samples receive different barcodes, thereby allowing for barcoding by sample rather than by cell.

The 5' common sequence can be selected as desired and can have various lengths. In some embodiments, the 5' common sequence has between 4-50 nucleotides in length. The barcode sequence itself can vary in length. In some embodiments, the barcode is between 5-50 or 5-75 nucleotides in length. A 3' capture sequence can vary depending on the sequences to be captured. In some embodiments, the capture sequence is a random sequence, e.g., a random sequence or 2, 3, 4, 5, 6, 7, 8, 9, 10, 15, 20 or more (e.g., 2-50, 2-25, 5-30) nucleotides. In some embodiments, the capture sequence is a homo-polymeric sequence (e.g., a polyA or a polyT sequence) of 2, 3, 4, 5, 6, 7, 8, 9, 10, 15, 20 or more (e.g., 2-50, 2-25, 5-30) nucleotides. In some embodiments, the capture sequence comprises a gene or target-specific capture sequence, for example of 2, 3, 4, 5, 6, 7, 8, 9, 10, 15, 20 or more (e.g., 2-50, 2-25, 5-30) nucleotides. In some embodiments, different barcoded oligonucleotides on the same cell can have different 3' capture sequences. This can be achieved for example by adding a mixture of 3' capture sequences to the oligonucleotides on the cells or nuclei.

A hydrogel is a network of polymer chains that are hydrophilic, sometimes found as a colloidal gel in which water is the dispersion medium. A three-dimensional solid results from the hydrophilic polymer chains being held together by cross-links. Cells or nuclei with barcode oligonucleotides attached can be mixed with a non-cross-linked (e.g., liquid) form of a hydrogel and then solidified (e.g., cross-linked). Exemplary hydrogels include but are not limited to those comprising alginate, agarose, nickel-nitrilotriacetic acid (Ni-NTA) agarose (which will bind dIMTP nucleosides), europium-nitrilotriacetic acid (Eu-NTA) agarose (which will bind dIMTP nucleosides), polyacrylamide, chitosan, hyaluronan, dextran, collagen, fibrin, polyethylene glycol (PEG), poly(hydroxyethyl methacrylate) (poly-HEMA), polyvinyl alcohol (PVA) or polycaprolactone (PCL). Concentrations of the hydrogel can be selected to provide a solid hydrogel to suspend the target cells. In some embodiments, the hydrogel concentration is between for example 0.1%-20%, e.g., 0.1-1, 0.1-10, 1-20, or 1-10% wt/vol. Cell concentration in the hydrogel can also be selected as desired. In some embodiment, the cell concentration is 10 cells/mL, 100 cells/mL, 1000 cells/mL, 10 000 cells/mL, 100 000 cells/mL, 1 000 000 cells/mL, 10 000 000 cells/mL, 100 000 000 cells/mL and 1 000 000 000 cells/mL or ranges between any two of the listed values (e.g., 10-100 000 000 cells/mL).

In some aspects, the hydrogel comprises polyacrylamide and the barcode oligonucleotides comprise a 3' acrydite phosphoramidite moiety, allowing for later linking of the moiety to the solidified acrylamide. This allows for immobilization of the barcode oligonucleotides at the cell membrane (or nuclear membrane)/hydrogel interface. See, e.g., Rehman, et al., *Nuc. Acids Res.* 27(20) 649-655 (1999).

In other embodiments, the hydrogel can be linked to a molecule having binding affinity for the barcode oligonucleotides. These can be used to better anchor the barcode oligonucleotides to the hydrogel/cell interface once the oligonucleotides are released from the cell. In some embodiments, the molecule has affinity to a nucleic acid sequence in the oligonucleotide. In some embodiments, the molecule has affinity to an affinity partner moiety linked to the oligonucleotide. Exemplary molecules having binding affinity include but are not limited to biotin, streptavidin, an antibody, an aptamer or a polynucleotide comprising a sequence of at least 6 (e.g., at least 8, 10, 12, 15, 20, e.g., 6-20 or more) contiguous nucleotides that is fully complementary to a sequence in the heterologous barcoded oligonucleotides. In embodiments where the molecule is biotin the barcode oligonucleotide is attached to streptavidin (or other avidin analog). In embodiments where the molecule is streptavidin the barcode oligonucleotide is attached to biotin. In embodiments where the molecule is an antibody or an aptamer, the barcode oligonucleotide will be linked to a moiety (e.g., a protein or non-protein antigen) to which the antibody or aptamer specifically binds.

Once the cells are embedded in the solidified hydrogel, hydrogel cross-linkage is initiated to form a solid hydrogel surrounding the cells. Initiating solidification of the hydrogel will depend on the type of hydrogel used. Generally methods of initiating cross-linkage of hydrogels is known. For example, agarose can be cross-linked when treated with calcium. Polyacrylamide can be polymerized with cross-linkers such as N,N'-Bis(acryloyl)cystamine and the reaction can be initiated by contacting the hydrogel with TEMED and ammonium persulfate (APS).

After the cells are embedded in the solidified hydrogel, the barcode oligonucleotides attached to the cells can be released. Because the hydrogel is solidified around the cells, the released oligonucleotides should not diffuse very far from the membrane/hydrogel interface. Indeed, in embodiments where the hydrogel comprises molecules with affinity to the oligonucleotides, diffusion should be further reduced thereby localizing the oligonucleotides at or near the cell membrane/hydrogel interface.

Release of the oligonucleotide from the cells can occur in any number of ways. In some embodiments, the oligonucleotides are cleaved from the cell membranes. Cleavage can occur by contacting the oligonucleotides with an enzyme that cleaves the oligonucleotides from the cells, e.g., in a sequence-specific manner of by cleaving a moiety that is part of the linkage of the oligonucleotide to the cell membrane.

In some embodiments, the release of the oligonucleotides is achieved by lysis of the cells. Lysis can occur by, for example, introduction of one or more reagents into the hydrogel to achieve lysis. Exemplary reagents can include, for example, an ionic or non-ionic detergent, a protease (e.g., proteinase K), or both.

In some embodiments, release of the barcodes is achieved without lysing the cells or nuclei. In some of these embodiments, intact cells or nuclei can be permeabilized to allow entry of reagents. Exemplary reagents can include the use of digitonin, or fixatives such as methanol, or paraformaldehyde.

Once released from the cells or nuclei, the barcode oligonucleotides are attached covalently or non-covalently to cellular or nuclear polynucleotides (e.g., genomic DNA, mRNA, small RNAs) or copies thereof (e.g., cDNAs). In embodiments in which the barcode oligonucleotides comprise a 3' capture sequence, cellular or nuclear polynucleotides or copies thereof can be hybridized to the barcode oligonucleotides and a polymerase can be added to the hydrogel to extend the barcode oligonucleotide in a template-dependent manner using the cellular polynucleotides as templates. In some embodiments, the 3' capture sequence is a polyT sequence and a reverse-transcriptase is used to form a first-strand cDNA from cellular RNA. In other embodiments, the lysed cells have been contacted with a reverse transcriptase and primer to form a first strand cDNA and then the barcode oligonucleotide is extended using the first strand cDNA as a template. In some embodiments, the cellular or nuclear polynucleotides are hybridized to the cellular barcodes and thus the barcodes and the cellular polynucleotides are linked at this point non-covalently. In other embodiments, the barcode oligonucleotides can be ligated to cellular or nuclear polynucleotides either directly or following enzymatic cleavage and/or polishing of ends of the cellular polynucleotides. In any case, because the barcoded oligonucleotides are localized to the cells from which they were released, the barcode oligonucleotides will be attached to polynucleotides or copies thereof of the cell or nucleus from which they were released. This allows for cell-specific barcoding of a cell's or nucleus's polynucleotides. Because a number of cells or nuclei are present in the hydrogel, this occurs in parallel in each cell or nucleus in the hydrogel without the formation of partitions (e.g., without formation of droplets, microfluidic channels, microwells, etc.). Moreover, a 1:1 ratio of barcode to cell is readily achieved in the methods described herein achieved, in contrast to the difficulties that can occur when attempting 1:1 delivery of different reagents, cells, etc., into partitions.

Once the cellular (or nuclear) polynucleotides are associated with the barcode oligonucleotides, the resulting barcoded cell polynucleotides can be released from the solidified hydrogel, for example by extraction (for example by electrophoresis) or melting of the hydrogel. In some embodiments, the hydrogel can be melted, thereby releasing and pooling the barcoded cellular polynucleotides. The hydrogel melting can be achieved as desired so long as the attachment of the barcode oligonucleotide to the cellular or nuclear polynucleotide is not disrupted. Melting conditions can include for example raising the temperature or contacting the hydrogel with one or more reagents that depolymerizes the gel. Exemplary depolymerizing reagents can include reducing agents such as dithiothreitol (DTT) or Tris(2-carboxyethyl)phosphine (TCEP).

One can subsequently analyze the resulting pool of barcoded polynucleotides as desired. In some embodiments, the polynucleotides can be nucleotide sequenced. By detecting the barcode sequence associated with the linked polynucleotide, one can determine from which cell each sequencing read came from. In some embodiments, one can sort sequencing reads by their barcode. For example, one can determine the relative amounts of a gene product in different cells, where different cells gene products are identified by having different barcodes.

Methods for high throughput sequencing and genotyping are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety.

Exemplary DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No. WO 2006/084,132, herein incorporated by reference in its entirety). In some embodiments, DNA sequencing is achieved by parallel oligonucleotide extension (See, e.g., U.S. Pat. Nos. 5,750,341; and 6,306,597, both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511,803; herein incorporated by reference in their entireties), the 454 picotiter pyrosequencing technology (Margulies et al., 2005 Nature 437, 376-380; U.S. Publication No. 2005/0130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbial., 7:287-296; U.S. Pat. Nos. 6,210,891; and 6,258,568; each herein incorporated by reference in its entirety), template DNA is fragmented, end-repaired, ligated to adapters, and clonally amplified in-situ by capturing single template molecules with beads bearing oligonucleotides complementary to the adapters. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10.\text{sup}.6$ sequence reads can be achieved, resulting in up to 500 million base pairs (Mb) of sequence.

In the Solexa/Illumina platform (Voelkerding et al., Clinical Chem., 55. 641-658, 2009; MacLean et al., Nature Rev. Microbial., 7:287-296; U.S. Pat. Nos. 6,833,246; 7,115,400; and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adapter oligonucleotides, which are subsequently used to capture the template-adapter molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbial., 7:287-296; U.S. Pat. Nos. 5,912,148; and 6,130,073; each herein incorporated by reference in their entirety) also involves fragmentation of the template, ligation to oligonucleotide adapters, attachment to beads, and clonal amplification by emulsion PCR. Following this, beads bearing template are immobilized on a derivatized surface of a glass flow-cell, and a primer complementary to the adapter oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In some embodiments, nanopore sequencing is employed (See, e.g., Astier et al., J. Am. Chem. Soc. 2006 Feb. 8; 128(5)1705-10, incorporated by reference). The theory behind nanopore sequencing relates to what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In some embodiments, HeliScope by Helicos BioSciences is employed (Voelkerding et al., Clinical Chem., 55. 641-658, 2009; MacLean et al., Nature Rev. Microbial, 7:287-296; U.S. Pat. Nos. 7,169,560; 7,282,337; 7,482,120; 7,501, 245; 6,818,395; 6,911,345; and 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (See, e.g., Science 327 (5970): 1190 (2010); U.S. Pat. Appln. Pub. Nos. 2009/0026082; 2009/0127589; 2010/0301398; 2010/0197507; 2010/0188073; and 2010/0137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is .about.99.6% for 50 base reads, with about 100 Mb generated per run. The read-length is 100 base pairs. The accuracy for homopolymer repeats of 5 repeats in length is about 98%. The benefits of ion semiconductor sequencing are rapid sequencing speed and low upfront and operating costs.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 2009/0035777, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; and U.S. patent application Ser. No. 11/671,956; and Ser. No. 11/781,166; each herein incorporated by reference in their entirety) in which immobilized, primed DNA template is subjected to strand extension using a fluorescently-modified polymerase and fluorescent acceptor molecules, resulting in detectible fluorescence resonance energy transfer (FRET) upon nucleotide addition.

Another real-time single molecule sequencing system developed by Pacific Biosciences (Voelkerding et al., Clinical Chem., 55. 641-658, 2009; MacLean et al., Nature Rev. Microbiol., 7:287-296; U.S. Pat. Nos. 7,170,050; 7,302,146; 7,313,308; and 7,476,503; all of which are herein incorporated by reference) utilizes reaction wells 50-100 nm in diameter and encompassing a reaction volume of approximately 20 zeptoliters (10.sup.-21 L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In some embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters (10.sup.-21 L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. Nos. 7,405,281; 7,315,019; 7,313, 308; 7,302,146; and 7,170,050; and U.S. Pat. Pub. Nos. 2008/0212960; 2008/0206764; 2008/0199932; 2008/ 0199874; 2008/0176769; 2008/0176316; 2008/0176241; 2008/0165346; 2008/0160531; 2008/0157005; 2008/ 0153100; 2008/0153095; 2008/0152281; 2008/0152280; 2008/0145278; 2008/0128627; 2008/0108082; 2008/ 0095488; 2008/0080059; 2008/0050747; 2008/0032301; 2008/0030628; 2008/0009007; 2007/0238679; 2007/ 0231804; 2007/0206187; 2007/0196846; 2007/0188750; 2007/0161017; 2007/0141598; 2007/0134128; 2007/

0128133; 2007/0077564; 2007/0072196; and 2007/0036511; and Korlach et al. (2008), "Selective aluminum passivation for targeted immobilization of single DNA polymerase molecules in zero-mode waveguide nanostructures," PNAS 105(4): 1176-81, all of which are herein incorporated by reference in their entireties.

EXAMPLE 1

Cell Partitioning and Barcoding in Reversible Polyacrylamide Matrix.

K562 and HEK 3T3 cells are resuspended in a one to one mix and anchored with modified L(ipid) M(odified) O(ligonucleotides). This is adapted from McGinnis et al (2019) with the following modification. The 3' end of the Anchor oligo is modified with acrydite phosphoramidite.

Clonal cell oligo barcode sequences are built on the LMOs as shown in FIG. 1 through split pool synthesis. 1 million of these mixed cells are combined in a volume of approximately 100 µL of PBS 1× buffer. This cell suspension is mixed with an equal volume of 12:1 Polyacrylamide: Bac (N,N'-Bis(acryloyl)cystamine) to form a 2% polyacrylamide gel suspension. After mixing thoroughly with a pipette, Ammonium persulfate and TEMED are added to produce a final concentration of 0.05% and 0.1%, respectively. The mixture is further pipette mixed and the approximately 200 µL of solution is deposited in an Eppendorf tube to allow for polyacrylamide solidification. The acrydite moiety on the Anchor portion of the LMOs will be incorporated in the polyacrylamide matrix during solidification to produce a sphere of oligonucleotides at the cell membrane/hydrogel matrix interface. Once the polyacrylamide is solidified, a cell lysis reagent, such as 0.1% NP40, is added to lyse the cells. Reverse transcription reagents are added and once the released mRNA binds to the PolyT track of the PolyT primer, primer template reverse transcription occurs to produce barcoded cDNA. DTT is added to a final concentration of 100 mM to dissolve the Polyacrylamide: BAC matrix to release the barcoded cDNA. The cDNA is collected, purified, concentrated and converted into an NGS library by standard methods.

EXAMPLE 2

Cell Partitioning and Barcoding in Reversible Agarose Matrix

K562 and HEK 3T3 cells are resuspended in a one to one mix and anchored with modified L(ipid) M(odified) O(ligonucleotides). This is adapted from McGinnis et al (2019) with the following modification. The 3' end of the Anchor oligo is modified with imidazole triphosphate nucleosides (dImTP).

Clonal cell oligo barcode sequences are built on the LMOs as shown in FIG. 2 through split pool synthesis. 1 million of these mixed cells are combined in a volume of approximately 100 µL of PBS 1× buffer. This cell suspension is mixed with an equal volume of 2% molten Ni-NTA or Eu-NTA agarose to form a 1% agarose gel suspension. After mixing thoroughly the approximately 200 µL of solution is deposited in an Eppendorf tube and the temperature is dropped to allow for agarose solidification. The dImTP on the anchor portion of the LMOs will bind to the Ni-NTA—or Eu-NTA agarose during solidification to produce a sphere of oligonucleotides at the cell membrane/hydrogel matrix interface. Once the agarose is solidified, a cell lysis reagent, such as 0.1% NP40, is added to lyse the cells. Reverse transcription reagents are added and once the released mRNA binds to the PolyT track of the PolyT primer, primer template reverse transcription occurs to produce barcoded cDNA. The agarose is heated to melt the matrix and release the barcoded cDNA. The cDNA is collected, purified, concentrated and converted into an NGS library by standard methods.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of tagging cell-specific barcodes to cell nucleic acids, the method comprising,
providing (i) cells or isolated cell nuclei having heterologous barcoded oligonucleotides attached to cell membranes of the cells or (ii) cell nuclei comprising heterologous oligonucleotides attached to nuclear membranes of the individual cell nuclei;
mixing the cells or nuclei with a liquid-form hydrogel;
cross-linking the hydrogel around the cells or nuclei, wherein the hydrogel forms a solid gel;
releasing the heterologous barcoded oligonucleotides from the cell membranes or nuclear membranes to generate released heterologous barcoded oligonucleotides;
allowing the heterologous barcoded oligonucleotides released from the cell membranes or nuclear membranes to locate at solidified hydrogel surrounding the cells or nuclei;
attaching the heterologous barcoded oligonucleotides to cell polynucleotides or copies or cDNAs thereof to form barcoded cell polynucleotides;
dissolving the solidified hydrogel or extracting the barcoded cell polynucleotides from the solidified hydrogel, thereby releasing barcoded cell polynucleotides from the hydrogel, thereby tagging cell-specific barcodes to cell nucleic acids.

2. The method of claim 1, wherein the allowing comprises binding the heterologous barcoded oligonucleotides released from the cell membranes or nuclear membranes to the solidified hydrogel surrounding the cells or nuclei.

3. The method of claim 1, wherein the heterologous barcoded oligonucleotides comprise a lipid moiety and wherein the lipid moiety anchors the heterologous barcoded oligonucleotides in the cell membranes or nuclear membranes.

4. The method of claim 1, wherein the hydrogel is covalently linked to a molecule having binding affinity for the heterologous oligonucleotides.

5. The method of claim 4, wherein the molecule is selected from the group consisting of biotin, streptavidin, an antibody, an aptamer, Ni, Eu, or a polynucleotide comprising a sequence of at least 6 contiguous nucleotides that is fully complementary to a sequence in the heterologous barcoded oligonucleotides.

6. The method of claim 5, wherein the nuclei comprise fragmented nuclear DNA, wherein the fragmented DNA comprises common adapter sequences at ends of the fragments.

7. The method of claim 6, wherein the method further comprises fragmenting the nuclear DNA and introducing the common adapter sequence with a transposase.

8. The method of claim 1, wherein the hydrogel is covalently linked to a molecule having binding affinity for the heterologous barcoded oligonucleotides and the released heterologous barcoded oligonucleotides bind to the molecule at a hydrogel/cell interface or hydrogel/nuclei interface.

9. The method of claim 1, wherein the releasing comprises cleaving the heterologous barcoded oligonucleotides from a portion of the oligonucleotides to free the heterologous barcoded oligonucleotides from the cell membrane or nuclear membrane.

10. The method of claim 1, wherein the attaching comprises ligating the heterologous barcoded oligonucleotides to cell polynucleotides or copies or cDNAs thereof to form the barcoded cell polynucleotides.

11. The method of claim 1, wherein the providing comprises synthesizing the heterologous barcoded oligonucleotides on the cells or nuclei using a split and pool methodology such that different cells or different nuclei are linked to a plurality of identical heterologous barcoded oligonucleotides and where different cells or different nuclei have unique heterologous barcoded oligonucleotides.

12. The method of claim 1, wherein the allowing comprises diffusion of the heterologous barcoded oligonucleotides released from the cell membranes or nuclear membranes to the solidified hydrogel surrounding the cells or nuclei such that the heterologous barcoded oligonucleotides are localized at a hydrogel/membrane interface.

13. The method of claim 1, wherein the extracting the barcoded cell polynucleotides from the solidified hydrogel comprises electrophoresing the barcoded cell polynucleotides from the solidified hydrogel.

14. The method of claim 1, further comprising sequencing the barcoded cell polynucleotides released from the hydrogel.

15. The method of claim 1, wherein the cells are mammalian cells.

16. The method of claim 1, wherein the hydrogel comprises alginate, agarose, polyacrylamide, chitosan, hyaluronan, dextran, collagen, fibrin, polyethylene glycol (PEG), poly(hydroxyethyl methacrylate) (polyHEMA), polyvinyl alcohol (PVA) or polycaprolactone (PCL).

17. The method of claim 1, wherein the hydrogel comprises alginate and the crosslinking comprises contacting the hydrogel with calcium.

18. The method of claim 12, wherein the molecule is streptavidin and the heterologous barcoded oligonucleotides biotinylated.

19. The method of claim 12, wherein the molecule is a polynucleotide comprising a sequence of at least 6 contiguous nucleotides that is fully complementary to a sequence in the heterologous barcoded oligonucleotides such that the polynucleotide linked to the hydrogel hybridizes to the released heterologous barcoded oligonucleotides.

20. The method of claim 1, wherein the releasing comprises lysing the cells or nuclei.

* * * * *